US011035809B2

(12) United States Patent
Awano et al.

(10) Patent No.: US 11,035,809 B2
(45) Date of Patent: Jun. 15, 2021

(54) THERMAL DIFFUSION FACTOR MEASUREMENT DEVICE, THERMAL DIFFUSION FACTOR MEASUREMENT METHOD AND PROGRAM

(71) Applicants: BETEL CO. LTD., Ibaraki (JP); NATIONAL UNIVERSITY CORPORATION NAGOYA UNIVERSITY, Aichi (JP)

(72) Inventors: Takaaki Awano, Ibaraki (JP); Kimihito Hatori, Ibaraki (JP); Makoto Sekine, Ibaraki (JP); Takahiko Kubota, Ibaraki (JP); Hosei Nagano, Aichi (JP); Ryohei Fujita, Aichi (JP)

(73) Assignees: BETEL CO. LTD., Ibaraki (JP); NATIONAL UNIVERSITY CORPORATION NAGOYA UNIVERSITY, Aichi (JP)

( * ) Notice: Subject to any disclaimer, the term of this patent is extended or adjusted under 35 U.S.C. 154(b) by 278 days.

(21) Appl. No.: 16/091,805

(22) PCT Filed: Apr. 5, 2017

(86) PCT No.: PCT/JP2017/014223
§ 371 (c)(1),
(2) Date: Oct. 5, 2018

(87) PCT Pub. No.: WO2017/175795
PCT Pub. Date: Oct. 12, 2017

(65) Prior Publication Data
US 2019/0162683 A1    May 30, 2019

(30) Foreign Application Priority Data
Apr. 6, 2016 (JP) .............................. JP2016-076616

(51) Int. Cl.
*G01N 25/18* (2006.01)
*G01N 33/00* (2006.01)

(52) U.S. Cl.
CPC ............. *G01N 25/18* (2013.01); *G01N 33/00* (2013.01); *G01N 2033/0003* (2013.01)

(58) Field of Classification Search
CPC combination set(s) only.
See application file for complete search history.

(56) References Cited

U.S. PATENT DOCUMENTS

| 2005/0002435 A1* | 1/2005 | Hashimoto | ............ G01N 25/72 374/43 |
| 2007/0143061 A1* | 6/2007 | Ringermacher | ....... G01N 25/18 702/136 |

FOREIGN PATENT DOCUMENTS

| EP | 2840385 A1 * | 2/2015 | .......... G01N 25/005 |
| JP | 2014-160038 A | 9/2014 | |
| JP | 2015-108546 A | 6/2015 | |

OTHER PUBLICATIONS

Vavilov et al., "Review of pulsed thermal NDT: Physical principles, theory and data processing", NDT&E International, vol. 73, pp. 28-52, 2015. (Year: 2015).*

(Continued)

*Primary Examiner* — Lisa M Caputo
*Assistant Examiner* — Nasir U. Ahmed
(74) *Attorney, Agent, or Firm* — Taro Yaguchi (57) ABSTRACT

To provide a thermal diffusion factor measurement device, a thermal diffusion factor measurement method and a program capable of measuring thermal diffusion with high accuracy, even when an object to be measured has anisotropy in which thermal diffusion factors differ greatly between the in-plane direction and the thickness direction and a thick thickness. In a thermal diffusion factor measurement method, a heating location H on a tabular sample is made to generate periodi- (Continued)

cally varying thermal waves and the thermal waves at a detection location S on the sample are detected by a non-contact temperature sensor. In addition, the phase delay of the thermal waves at the detection location S is detected in consideration of a detection sensitivity distribution DS of the non-contact temperature sensor and the thermal diffusion factor in the in-plane direction of the sample is measured using the phase delay.

8 Claims, 3 Drawing Sheets

(56) References Cited

OTHER PUBLICATIONS

Takahiro Shinohara et. al., "Thermowave Analyzer o Mochiita Fukugo Zairyo no Netsu Kakusanritsu Sokutei", The Japan Institute of Metals 2016 Nen (Dai 158 Kai) Shunki Koen Taikai Koen Gaiyoshu, Mar. 9, 2016 (Mar. 9, 2016), p. 133.

* cited by examiner

THERMAL DIFFUSION FACTOR MEASUREMENT DEVICE, THERMAL DIFFUSION FACTOR MEASUREMENT METHOD AND PROGRAM

FIELD OF THE INVENTION

The present invention relates to a thermal diffusion factor measurement device, a thermal diffusion factor measurement method and a program.

BACKGROUND OF THE INVENTION

Carbon fiber-reinforced composite materials have recently been used in electronic devices and others as materials having high thermal conductivity, anisotropy and high specific rigidity. It is known that there occurs a big difference in the thermal diffusion factor in such carbon fiber-reinforced composite materials due to anisotropy generated by the orientation of carbon fibers.

In carbon fiber-reinforced composite materials, the thermal diffusion factor in the in-plain direction is higher, because fibers are generally oriented in the in-plain direction of materials. While carbon fiber-reinforced composite materials for heat dissipation are used for dissipating heat from CPUs and batteries due to the miniaturization of electronic devices, such materials used for heat dissipation also have a high thermal diffusion factor in the in-plain direction, because strong atomic bonds are arranged in the in-plain direction.

In general thermal dissipation factor measurement methods, isotropic materials are targeted that have identical thermal diffusion factors both in the in-plain direction and the thickness direction, i.e., it is not considered that thermal diffusion requires additional time in the thickness direction. Accordingly, in general thermal dissipation factor measurement methods, it is not possible to find accurate values in samples having a thickness of 100 μm or more and being anisotropic.

Aa a thermal diffusion factor measurement method for this type of materials having anisotropy, a non-patent literature (Hosei Nagano, Hideyuki Kato, Akira Onishi, Yuji Nagasaka, "Thermal diffusivity measurement of anisotropic graphite sheets by a laser heating-type AC calorimetry technique", National Heat Transfer Symposium, collected papers, $37^{th}$, Vol. 3, p 901-902, published in 2000) discloses a method using an AC calorimetry technique. In this thermal diffusion factor measurement method, a three-dimensional theory is applied to analyze the thermal diffusion factor simultaneously in the in-plain direction as well as in the thickness direction by fitting the solution to its heat conduction equation to measurement results.

Furthermore, a patent literature (Japanese Patent Application Kokai Publication No. 2015-108546) also discloses a thermal diffusion factor measurement device developed by the present inventors. The thermal diffusion factor measurement device disclosed in the non-patent literature heats the front face of a tabular object to be measured using laser spot periodic heating, detects a change in temperature on the rear face of the object to be measured, and calculates a phase delay between the change in temperature and the heating cycle to find the thermal diffusion factor of the object to be measured on the basis of the calculated phase delay.

SUMMARY OF THE INVENTION

In the thermal diffusion factor measurement method according to the abovementioned non-patent literature, the sample temperature is measured using a thermocouple that is fixed to the sample with silver paste, and therefore the fixation or removal of the thermocouple to or from the sample is complicated. A thermocouple used for this type of measurement is so thin that much care is required for handling the thermocouple. As a result, measurement errors caused by sample preparation or operators are also significant.

Hence, in place of a thermocouple, it can be contemplated to use a radiation thermometer with InSb as a detection element that is capable of measuring the sample temperature in a non-contact manner. In such a radiation thermometer, however, the thermometer is disposed with a space from a sample; therefore, the problem is that the accuracy is low, because the alternating current temperature of a sample is measured for so wide an area due to the configuration of an optical system.

On the other hand, in the thermal diffusion factor measurement method according to the abovementioned patent literature, it is possible to accurately measure the thermal diffusion factor in the in-plane direction as well as the thermal diffusion factor in the thickness direction for the carbon fiber-reinforced composite material having a thickness of about 130 μm. However, there is recently a need to measure an object to be measured so much thicker that even the thermal diffusion factor measurement device described in the abovementioned patent literature might be difficult to handle it.

Accordingly, the object of the present invention is to provide a thermal diffusion factor measurement device, a thermal diffusion factor measurement method and a program capable of suppressing a decline in accuracy even when a temperature is detected in non-contact manner. Furthermore, the other object of the present invention is to provide a thermal diffusion factor measurement device, a thermal diffusion factor measurement method and a program capable of measuring thermal diffusion with high accuracy, even when an object to be measured has anisotropy in which thermal diffusion factors differ greatly between the in-plane direction and the thickness direction and a thick thickness.

In order to achieve the abovementioned objects, the thermal diffusion factor measurement device according to the present invention is characterized by comprising heating unit for periodically heating a heating location on a front face of an object to be measured in a non-contact manner, the object having the front face and a rear face, a non-contact temperature sensor for detecting the temperature of a detection location on the rear face of the object in a non-contact manner, and a thermal diffusion factor computing unit for calculating a phase delay of a temperature cycle detected by the non-contact temperature sensor relative to a heating cycle generated by the heating unit, and computing a thermal diffusion factor of the object based on the calculated phase delay, wherein the thermal diffusion factor computing unit obtains an intensity of a detection sensitivity distribution at the detection location with respect to the temperature detected by the non-contact temperature sensor, subjects a phase of the detected temperature cycle at the detection location and the obtained intensity of the detection sensitivity distribution to integral processing, and thereby calculates a phase delay at the detection location to compute the thermal diffusion factor of the object.

Furthermore, the thermal diffusion factor measurement method according to the present invention is a method for measuring a thermal diffusion factor of an object to be measured having a front face and a rear face by heating the front face of the object and detecting a temperature of the rear face of the object, wherein the method is characterized by comprising a heating step of periodically heating a heating location on the front face of the object in a non-contact manner, a temperature detecting step of detecting a temperature of the detection location on the rear face of the object in a non-contact manner, and a computing step of calculating a phase delay of a temperature cycle detected at the temperature detecting step relative to a heating cycle at the heating step, and then computing a thermal diffusion factor of the object based on the calculated phase delay, wherein, in the computing step, the intensity of a detection sensitivity distribution at the detection location is obtained with respect to the temperature detected at the temperature detection step, and a phase of the detected temperature cycle at the detection location and the obtained intensity of the detection sensitivity distribution are subjected to integral processing to thereby calculate the phase delay at the detection location, so that the thermal diffusion factor of the object to be measured can be computed.

The present inventors found that thermal diffusion factors could accurately be measured both in the in-plane direction and in the thickness direction, even when an object to be measured had anisotropy in which thermal diffusion factors differed greatly between the in-plane direction and the thickness direction and a thick thickness, by computing the thermal diffusion factors using values found by subjecting not only the temperature of a specific measurement point but also temperatures in its surrounding to integral processing at the time of detecting the temperature of the object to be measured. In view of the abovementioned finding, the thermal diffusion factor measurement device and measurement method according to the present invention obtains detection temperatures within the range of the detection sensitivity distribution centering around the detection location and subjects the phase of a detection temperature cycle and the detection temperatures within the detection sensitivity distribution at the detection location to integral processing to thereby calculate a phase delay at the detection location, so that the thermal diffusion factor of the object to be measured can be computed. Here, the object to be measured may be tabular, rod-like or has any other shape as long as it has the front face and the rear face.

Furthermore, in the thermal diffusion factor measurement device and measurement method according to the present invention, the detection temperature within the detection sensitivity distribution is preferably found on the basis of the full width at half maximum of the detection temperature at the detection location. According to the finding of the present inventors, the abovementioned constitution allows for measuring the thermal diffusion factor of an object to be measured more accurately both in the in-plane direction and in the thickness direction.

Furthermore, in the thermal diffusion factor measurement device according to the present invention, preferably, the heating unit is a laser irradiation part in which heating is performed by irradiating laser, and the laser irradiation part heats the heating location by Gaussian beams in which the intensity is modulated by a prescribed angular frequency. Furthermore, in the thermal diffusion factor measurement method according to the present invention, preferably, the heating location is heated by Gaussian beams in the heating step in which the intensity is modulated by a prescribed angular frequency.

At the time of heating an object to be measured by laser irradiation, computation is conventionally performed by regarding a heating location as a point. According to the finding of the present inventors, the intensity distribution in the in-plane direction substantially followed the Gaussian distribution, and therefore the laser irradiation was performed by Gaussian beams in which the intensity was modulated by a prescribed angular frequency. The abovementioned constitution allows for measuring the thermal diffusion factor of an object to be measured more accurately both in the in-plane direction and in the thickness direction.

Furthermore, the program for thermal diffusion factor measurement according to the present invention is a program for measuring the thermal diffusion factor of an object to be measured having the front face and the rear face, the program being performed by a computer, wherein the thermal diffusion factor of the object to be measured is measured using a thermal diffusion factor measurement device by heating the front face of the object to be measured and then detecting the temperature of the rear face of the object to be measured, wherein: the front face of the object to be measured is periodically heated by the thermal diffusion factor measurement device in a non-contact manner; the temperature of a detection location is detected on the rear face of the object to be measured in a non-contact manner, the intensity of a detection sensitivity distribution is found about the detected temperature at the detection location; and then the phase of the detection temperature cycle at the detection location and the intensity of the found detection sensitivity distribution are subjected to integral processing to thereby calculate a phase delay at the detection location between the heating cycle and the detection temperature cycle, so that the thermal diffusion factor of the object to be measured can be computed. The abovementioned program allows for carrying out the abovementioned thermal diffusion factor measurement device and thermal diffusion factor measurement method.

DETAILED DESCRIPTION OF THE INVENTION

Figure 1:
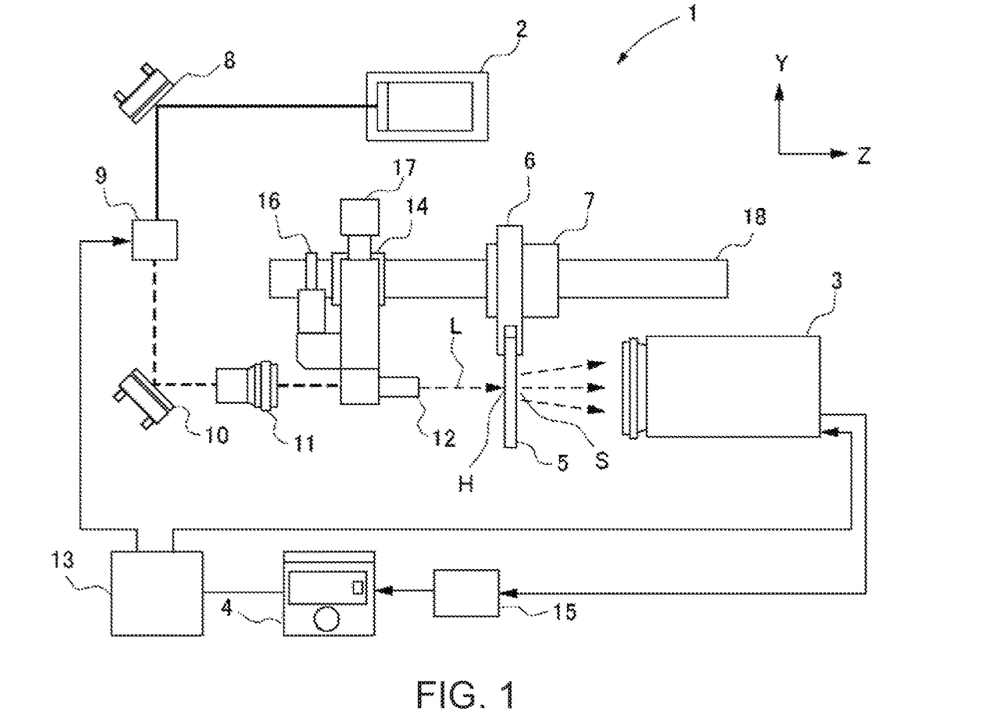
FIG. 1 is an explanatory view showing the constitution of a thermal diffusion factor measurement device according to the present embodiment.

The following describes one embodiment of the thermal diffusion factor measurement device, thermal diffusion factor measurement method and thermal diffusion factor measurement program according to the present invention with reference to drawings. As shown in FIG. 1, the thermal diffusion factor measurement device 1 according to the present embodiment comprises a laser irradiation part 2 as a heating unit, an infrared thermography 3 as a non-contact temperature sensor, and a computer 4 as a thermal diffusion factor measurement computing means. In the present embodiment, the computer 4 stores the program used for activating the thermal diffusion factor measurement device 1 and thereby performing the thermal diffusion factor measurement method.

Moreover, the thermal diffusion factor measurement device 1 comprises a holder 6 for holding a tabular sample 5, an object to be measured, and an XYZ stage 7 for moving the holder 6 in the X and Y directions (in-plane directions of the sample 5) as well as in the Z direction (thickness direction of the sample 5).

In the present embodiment, a semiconductor laser device is used for the laser irradiation part 2, which is disposed in such a way as to heat the front face of the sample 5 (the left-side face of the sample 5 in FIG. 1). At the time of irradiating a laser beam, the laser irradiation part 2 alters its intensity by changing the current supplied to the device.

In addition to the laser irradiation part 2, the heating unit comprises a first mirror 8, an acousto-optic device 9, a second mirror 10, a beam expander 11, and a microscope 12. The first mirror 8 and the second mirror 10 reflect a laser beam emitted from the laser irradiation part 2 and guide it to the beam expander 11. The acousto-optic device 9 is connected to a periodic signal generator 13 and is a device to which a periodic signal transmitted from the periodic signal generator 13 is inputted and which converts a laser beam generated by the laser irradiation part 2 to a periodic signal.

In the present embodiment, the frequency of a laser beam emitted from the laser irradiation part 2 is set to 0.005 Hz to 300 Hz. The beam expander 11 expands the beam diameter of the laser beam guided to the second mirror 10. The laser beam is finally irradiated to a heating location H on the front face of the sample 5 as a spot via the microscope 12 (see FIG. 2). Furthermore, in the present embodiment, it is configured that the laser beam irradiated to the heating location H of the sample 5 becomes a so-called Gaussian beam.

The Gaussian beam according to the present embodiment is formed by modulating the intensity of a laser beam by a prescribed angular frequency at the laser irradiation part 2. In the present embodiment, this angular frequency is set to $2\pi f$. By setting the angular frequency in this manner, thermal diffusion factors can be measured more accurately in the in-plane and thickness directions of an object to be measured.

The infrared thermography 3 is a device capable of obtaining heat generated from a surface of an object to be measured as an image in non-contact manner and then measuring the temperature from the image. In the present embodiment, the infrared thermography 3 is disposed in such a way that the temperature of a detection location S on the rear face of the sample 5 can be measured.

Moreover, the infrared thermography 3 is connected to the periodic signal generator 13 and the lock-in amplifier 15 and transmits temperature data to a computer 4 as a periodic signal via the lock-in amplifier 15. The lock-in amplifier 15 is a device used for detecting a phase delay of a heating cycle obtained by the infrared thermography 3 relative to a heating cycle generated by the laser irradiation part 2, on the basis of a temperature modulated signal transmitted from the infrared thermography 3 and a reference signal transmitted from the periodic signal generator 13.

The periodic signal generator 13 is a function generator capable of generating alternating current signals having any frequencies and waveforms. In the present embodiment, it is controlled by the computer 4 and transmits a periodic signal to the acousto-optic device 9 and the infrared thermography 3.

An LED 16 and a CCD camera 17 are configured to visually recognize the state of the front face of the sample 5 as an image via the microscope 12. The XYZ stage 7 and the XY stage 14 are mounted on a rail 18 provided at the thermal diffusion factor measurement device 1.

Next, the following describes the thermal diffusion factor measurement method using the thermal diffusion factor measurement device 1 with reference to FIGS. 1-6. In the present embodiment, the thermal diffusion factor measurement method is constituted of a heating step, a temperature detection step, and a computing step. First, a user making a measurement inputs parameter necessary to measure the thermal diffusion factor to the thermal diffusion factor measurement device 1. By way of example, the parameter includes laser frequency, laser power, distance between the microscope 12 and the sample 5, intervals of measurement points by the infrared thermography 3, sample thickness and external dimensions of the sample.

In the present embodiment, the sample 5, an object to be measured for which the thermal diffusion factor is measured, is made of a graphite sheet (carbon fiber-reinforced composite material) or CFRTP (carbon fiber-reinforced thermoplastic resin) and has anisotropy in the thermal diffusion factor, wherein the thermal diffusion factors ax and ay in the in-plane direction (X direction and Y direction) differ from the thermal diffusion factor az in the thickness direction (Z direction). The sample 5 used in the present embodiment has identical thermal diffusion factors in the X and Y directions.

Moreover, the size of the sample 5 is 50 mm in length (Len in FIG. 2), 50 mm in width (WID in FIG. 2) and 400 µm in thickness (d). In the present embodiment, the size of the sample 5 should be 10 mm or more both in length and width and large enough to be mounted on the thermal diffusion factor measurement device 1. The thickness of the sample 5 may be 0.01 mm to 2 mm.

In the heating step, a laser beam is irradiated from the laser irradiation part 2, reflected by the first mirror 8 and then introduced into the acousto-optic device 9. In the acousto-optic device 9, the laser beam is converted to a heating wave by a periodic signal transmitted from the periodic signal generator 13, which is controlled by the computer 4. After the acousto-optic device 9, the laser beam is reflected by the second mirror 10, has its beam diameter expanded and then irradiated to the heating location H on the front face of the sample 5 via the microscope 12.

In the temperature detection step, the temperature of the detection location S on the rear face of the sample 5 is detected by the infrared thermography 3 in a non-contact manner. In the infrared thermography 3, the temperature of the detection location S of the sample 5 is obtained as an image. The image data thus obtained is periodically-changing image data, because the heating location H is periodically heated by laser beams and thereby the temperatures of the heating location H and the detection location S alter periodically. To the infrared thermography 3 is inputted a periodic signal from the periodic signal generator 13, and it is transmitted to the computer 4 via the lock-in amplifier 15 together with the image data obtained.

The lock-in amplifier 15 continually captures image data obtained at the infrared thermography 3 and performs computation on the basis of a frame rate at constant intervals, which is optionally set, to generate image data averaged from the amount of continually changing temperature variation.

In the computing step, the computer 4 calculates a phase delay θ' between a heating cycle of laser beams used for heating the sample 5 in the heating step and a detection temperature cycle of the image data that is detected by the infrared thermography in the temperature detection step and then passes through the lock-in amplifier 15. Furthermore, the computer 4 finds the thermal diffusion factor of the sample 5 on the basis of the phase delay θ'.

Figure 2:
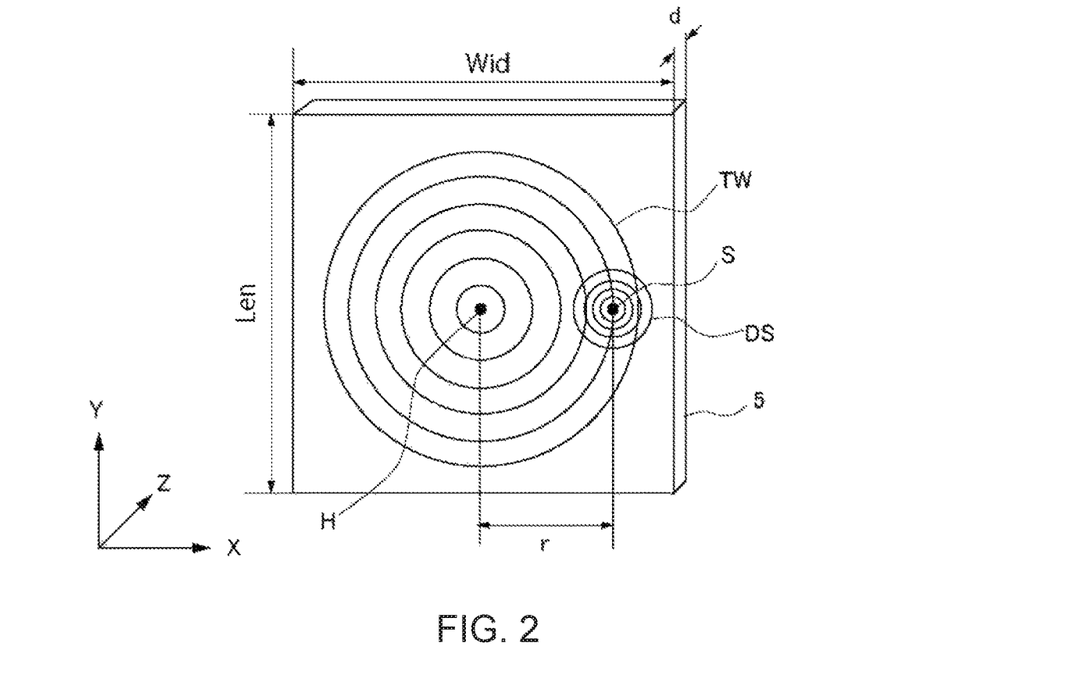
FIG. 2 is an explanatory view showing the state of a heating location and the state of a detection location when thermal waves are generated at the heating location of a sample.
Figure 3A:
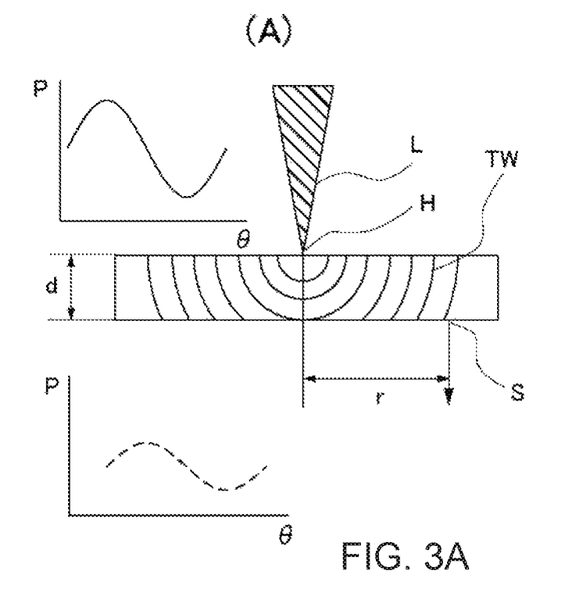
FIG. 3A is an explanatory view showing the state of thermal waves within a sample when a laser beam is irradiated to a heating location of the sample.
Figure 3B:
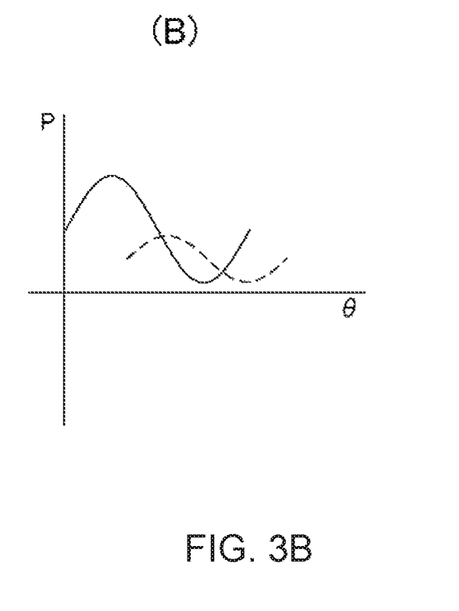
FIG. 3B an explanatory view showing a phase delay between a thermal wave detected at a detection location and a heating wave.

Next, in the thermal diffusion factor measurement method according to the present embodiment, the following describes the way of specifically finding the phase delay θ' and the thermal diffusion factor of the sample 5. As shown in FIGS. 2 and 3(A), a laser beam L emitted from the microscope 12 is irradiated to the heating location H on the front face of the sample 5. The laser beam L is a periodic heating wave, and a temperature wave TW is propagated inside the sample 3 and spread to its surrounding as shown in FIG. 2 and FIGS. 3A and 3B.

On the rear face of the sample 5, the temperature wave TW transferred from the heating location H is detected at the detection location S. At the detection location S, as shown in FIG. 3(A), the temperature wave TW generated by heating at the heating location H is detected with a phase delay. In the present embodiment, signals are also detected within the range of a certain detection sensitivity distribution DS, as shown in FIGS. 2 and 4.

Figure 4:
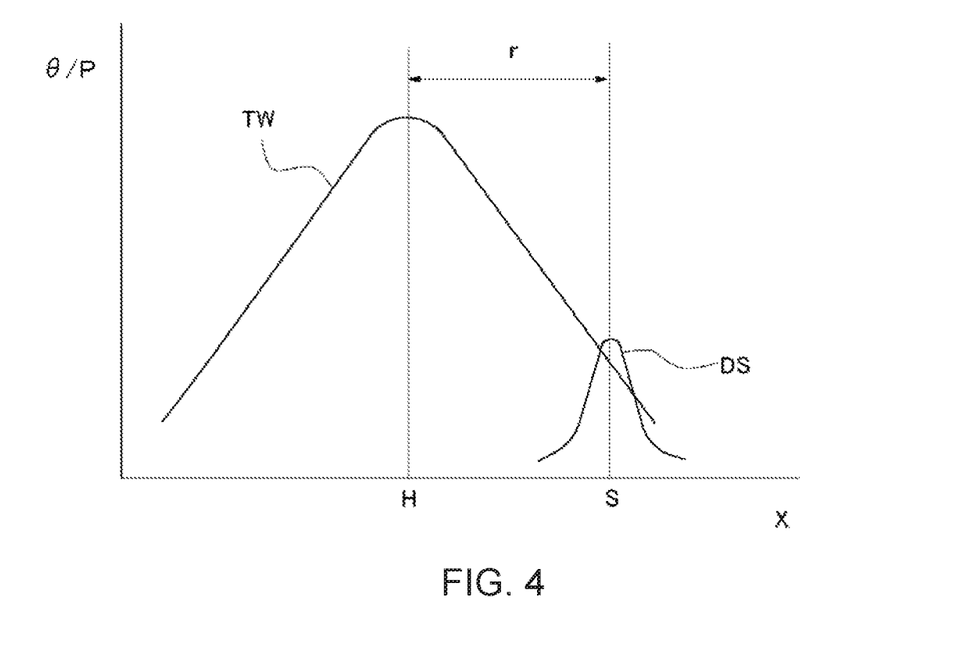
FIG. 4 is an explanatory view showing a phase delay of thermal waves and the intensity of detection sensitivity distribution at a detection location.

FIG. 4 is a schematic view showing the relationship between the phase delay θ of the temperature wave TW and the intensity P of the detection sensitivity distribution. As shown in FIG. 4, the temperature wave TW generated at the heating location H is attenuated as it is propagated inside the sample 5 and detected at the detection location S, wherein the infrared thermography 3 detects the temperature wave TW within a certain range (i.e., not at one point of the detection location S). The range is shown in FIG. 4 as the detection sensitivity distribution DS; as shown in FIG. 4, the detected temperature signal is bell-shaped with the center of the detection location S as its apex.

In this detection sensitivity distribution DS, the center coordinate (x', y', z') of the heating location H is set to the origin, and the center coordinate of the detection location S is set to (x, y, z). Here, the heating location H or the detection location S described hereinafter may include its center.

In the present embodiment, the sample 5 has identical thermal diffusion factors in the X and Y directions. Therefore, the thermal diffusion factor in the X direction (ax) is equivalent to the thermal diffusion factor in the Y direction (ay). In this case, the temperature T at a certain point in time (t) of the detection location can be expressed as the following Equation (1).

$$T(x, y, z, t) = \frac{1}{4\pi\sqrt{a_x a_z}\, l(x, y, z)} e^{i(\omega t - kl(x,y,z)) - kl(x,y,z)} \quad (1)$$

Here, l (x, y, z) in the Equation (1) is a thermal distance between the center coordinate of the heating location H and the center coordinate of the detection location S and can be expressed by the following Equation (2).

$$l(x, y, z) = \sqrt{(x-x')^2 + (y-y')^2 + \frac{a_x}{a_z}(z-z')^2} \quad (2)$$

The center coordinate (x', y', z') of the heating location H is the origin (i.e., zero), and therefore the following Equation (3) is established.

$$x'=y'=z'=0 \quad (3)$$

Here, k in Equation (1) is the wave number of a temperature wave having a frequency f, which is propagated inside the sample 5, and can be expressed by the following equation. Also, ω is the angular frequency at the time of heating modulation (2πf).

$$k = \sqrt{\frac{\pi f}{a_x}} \quad (4)$$

The phase θ of the detection temperature cycle at the detection location S is expressed by the following Equation (5). Here, l is a distance in the in-plane direction from the center coordinate (x', y', z') of the heating location H and is r in this embodiment. Also, k shows the wave number in Equation (5).

$$\theta(x,y,z)=kl(x,y,z) \quad (5)$$

The intensity P of the detection sensitivity distribution DS at the detection location S is expressed by the following Equation (6).

$$P = P(x, y) = \frac{1}{2\pi R^2} e^{-\frac{x^2+y^2}{2R^2}} \quad (6)$$

Here, R in Equation (6) is the standard deviation of the normal distribution of detected temperature signals and can be expressed by the following Equation (7). Also, W in Equation (7) is found on the basis of the full width at half maximum of the detection temperature distribution DS.

$$R = \frac{W}{2\sqrt{2\log_e 2}} \quad (7)$$

By subjecting the phase (θ) and the intensity P of the detection sensitivity distribution to convolutional integration, a phase delay (θ') in consideration of the detection sensitivity distribution is found by the following Equation (8).

$$\theta'(r,z)=\int_{-\infty}^{\infty}\int_{-\infty}^{\infty}\theta(x,y,z)P(x+r,y)dxdy \quad (8)$$

Thus, in the thermal diffusion factor measurement method according to the present embodiment, the abovementioned computing is performed by a program stored in the computer 4 as a computing means. The computer 4 performs the abovementioned computing at a plurality of measurement points, and the result is plotted on a graph shown in FIG. 5 (AR in FIG. 5). In this state, the thermal diffusion factor in the in-plane direction (ax values) and the thermal diffusion factor in the thickness direction (az values) are changed, and the thermal diffusion factor in the in-plane direction (ar) is found by fitting the values to a graph showing the relationship between the distance r in the X direction and the phase delay θ' found by measurement.

Figure 5:
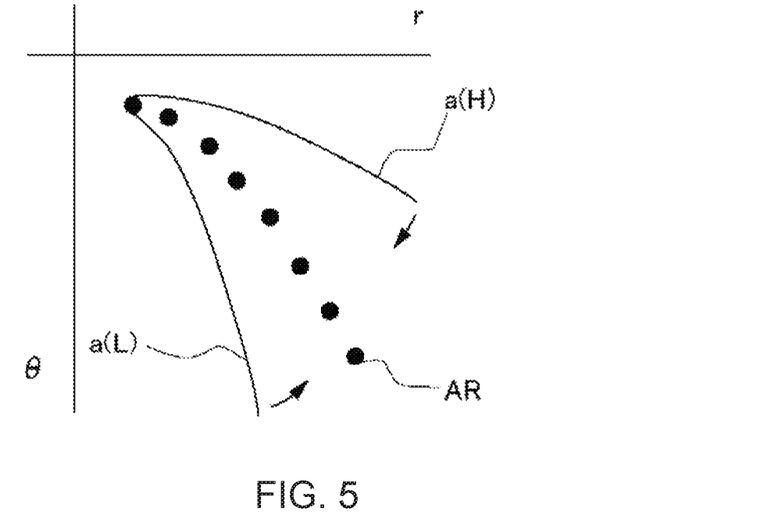
FIG. 5 is an explanatory view showing a way for finding the thermal diffusion factor by means of fitting using measured values of a phase delay.

In FIG. 5, curves a(H) and a(L) show results of measuring a sample having a known thermal diffusion factor by the thermal diffusion factor measurement device 1. The curve a(H) shows the state in which the thermal diffusion factor is high in the in-plane direction, and the curve a(L) shows the state in which the thermal diffusion factor is low in the in-plane direction. An arrow in the vicinity of the curve a(H) shows that fitting needs to be performed for making the thermal diffusion factor in the in-plane direction low, and an arrow in the vicinity of the curve a(L) shows that fitting needs to be performed for making the thermal diffusion factor in the in-plane direction high. In the present embodiment, the computer 4 performs computation for either of the abovementioned fitting methods, and the thermal diffusion factor of the sample 5 is found by finding a thermal diffusion factor of a straight line that fits well to a plotted measurement result.

Figure 6A:
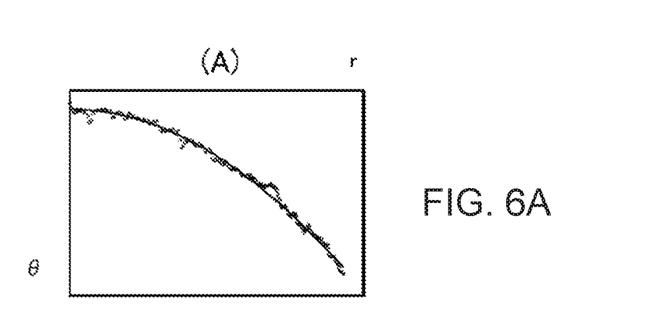
FIGS. 6A and 6B are explanatory views showing data when thermal diffusion factors were found by means of fitting.
Figure 6B:
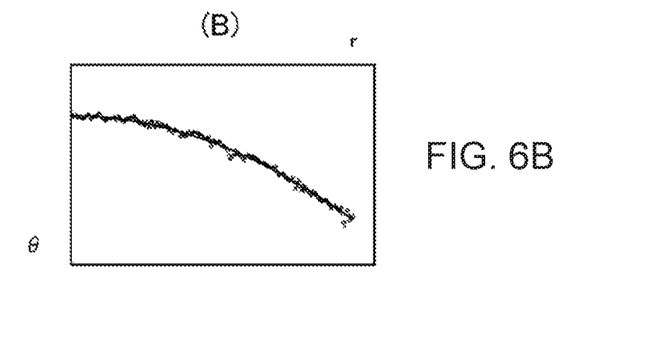

FIGS. 6A and 6B are explanatory views showing data obtained by finding the thermal diffusion factor of CFRTP by means of fitting according to the procedure shown in FIG. 5. FIG. 6A shows that measurement was made after setting the frequency of laser emitted from the laser irradiation part 2 to 0.01 Hz. FIG. 6B shows that measurement was made after setting the abovementioned frequency to 0.05 Hz.

In FIGS. 6A and 6B, black spots show actual measured values and solid lines show the results of fitting. In the thermal diffusion factor measurement device 1 according to the present embodiment, as clearly shown in FIGS. 6A and 6B, it was confirmed that fitting could successfully be performed for results measured with a plurality of frequencies for the same sample.

In each of the abovementioned embodiments, measurement methods are explained for the sample 5 having identical thermal diffusion factors ax and ay in the in-plane direction; however, in the case of samples having anisotropy in the thermal diffusion factor even in the in-plane direction as well, computation similar to that of the abovementioned embodiments can be performed by taking such anisotropy into consideration in the abovementioned calculation formulae. By way of example, the thermal diffusion factor in the Y direction (ay) can be calculated as a value found by multiplying ax by an anisotropic ratio.

Furthermore, although a graphite sheet or CFRTP is used as the sample 5 in the abovementioned embodiments, samples are not limited to those examples; the thermal diffusion factor may be measured for samples having no anisotropy as well as those having anisotropy. Moreover, the angular frequency of Gaussian beams is $2\pi f$ in the abovementioned embodiments; however, it is not limited to this value (i.e., other values may be used as well).

EXPLANATION OF REFERENCE NUMERALS

1: Thermal diffusion factor measurement device, 2: laser irradiation part, 3: infrared thermography (non-contact temperature sensor), 4: computer, 5: sample, 6: holder, 7: XYZ stage, 8: first mirror, 9: acousto-optic device, 10: second mirror, 11: beam expander, 12: microscope, 13: periodic signal generator, 14: XY stage, 15: lock-in amplifier, 16: LED, 17: CCD camera, 18: rail, H: heating location, L: laser beam, S: detection location, TW: thermal wave.

What is claimed is:

1. A thermal diffusion factor measurement device, comprising:
    a holder for holding an object having a front face and a rear face;
    a heating unit disposed to periodically heat in a non-contact manner a healing location on the front face of the object held by the holder;
    a non-contact temperature sensor disposed to detect in a non-contact manner a temperature of a detection location on the rear face of the object held by the holder: and
    a thermal diffusion factor computing unit for calculating a phase delay ($\theta'$) of a temperature cycle detected by the non-contact temperature sensor relative to a heating cycle by the heating unit, and computing a thermal diffusion factor of the object based on the calculated phase delay,
    wherein the thermal diffusion factor computing unit obtains an intensity (P) of a detection sensitivity distribution at the detection location with respect to the temperature detected by the non-contact temperature sensor, and subjects a phase ($\theta$) of the detected temperature cycle at the detection location and the obtained intensity of the detection sensitivity distribution to integration $\theta'(r,z)=\int_{-\infty}^{\infty}\int_{-\infty}^{\infty}\theta(x,y,z)P(x+r,y)dxdy$, and thereby computes the thermal diffusion factor of the object by line fitting the phase delay at a plurality of points with respect to in-plane directions (r).

2. The thermal diffusion factor measurement device according to claim 1, wherein the detected temperature within the detection sensitivity distribution is obtained from a full width at half maximum of the detected temperature at the detection location.

3. The thermal diffusion factor measurement device according to claim 2, wherein the heating unit is a laser irradiation part in which heating is performed by irradiation laser, and the laser irradiation part heats the heating location by Gaussian beams in which the intensity is modulated by a prescribed angular frequency.

4. The thermal diffusion factor measurement device according to claim 1, wherein the heating unit is a laser irradiation part in which heating is performed by irradiating laser, and the laser irradiation part heats the heating location by Gaussian beams in which the intensity is modulated by a prescribed angular frequency.

5. A method for measuring the thermal diffusion factor of an object to be measured, having a front face and a rear face; by heating the front face of the object and thereby detecting a temperature of the rear face of the object, the method comprising:
    a heating step of periodically heating a heating location on the front face of the object in a non-contact manner;
    a temperature detecting step of detecting a temperature of a detection location on the rear face of the object in a non-contact manner; and
    a computing step of calculating a phase delay ($\theta'$) of a temperature cycle detected at the temperature detecting step relative to a heating cycle at the heating step, and then computing the thermal diffusion factor of the object based on the calculated phase delay,
    wherein, in the computing step, an intensity (P) of a detection sensitivity distribution at the detection location is obtained with respect to the temperature detected at the temperature detection step, and a phase ($\theta$) of the detected temperature cycle at the detection location and the obtained intensity of the detection sensitivity distribution are subjected to integration $\theta'(r,z)=\int_{-\infty}^{\infty}\int_{-\infty}^{\infty}\theta(x,y,z)P(x+r,y)dxdy$, and the thermal diffusion factor of the object is obtained by the line fitting the phase delay at a plurality of points with respect to in-plane directions (r).

6. The thermal diffusion factor measurement method according to claim 5, the detected temperature within the detection sensitivity distribution is obtained based on a full width at half maximum of the detected temperature at the detection location.

7. The thermal diffusion factor measurement method according to claim 6, wherein, in the heating step, the heating location is heated by Gaussian beams in which the intensity is modulated by a prescribed angular frequency.

8. The thermal diffusion factor measurement method according to claim 5, wherein, in the heating step, the heating location is heated by Gaussian beams in which the intensity is modulated by a prescribed angular frequency.

* * * * *